United States Patent [19]
Barnes et al.
[11] Patent Number: 4,556,318
[45] Date of Patent: Dec. 3, 1985

[54] SPECTROCHEMICAL ANALYSIS

[75] Inventors: Ramon M. Barnes, Hadley, Mass.; Peter Fodor, Budapest, Hungary
[73] Assignee: Allied Corporation, Morristown, N.J.

[21] Appl. No.: 501,840
[22] Filed: Jun. 7, 1983
[51] Int. Cl.[4] .......... G01N 21/73
[52] U.S. Cl. .......... 356/316; 356/36
[58] Field of Search .......... 356/36, 312, 315, 316

[56] References Cited

U.S. PATENT DOCUMENTS

| | | | |
|---|---|---|---|
| 3,586,441 | 6/1971 | Smith et al. | 356/320 |
| 3,832,060 | 8/1974 | Dahlquist | 356/36 |
| 3,895,873 | 7/1975 | Dennison et al. | 356/85 |
| 4,367,042 | 1/1983 | Smith, Jr. et al. | 356/417 |

OTHER PUBLICATIONS

"Atomization Under Pressure in Graphite Furnace Atomic Absorption Spectrometry", Sturgeon, R. E. et al., *Spectrochimica Acta,* vol. 32B, p. 257, 1977.
"Gas Flow Dynamics of an Inductively Coupled Plasma Discharge", Barnes, R. M. et al., *Spectrochimica Acta,* vol. 36B, N.Y., p. 299, 1981.
Gunn, et al., *Analyst,* vol. 103, pp. 1066–1073, (Oct. 1978).
Millard, et al., *Analyst,* vol. 105, pp. 502–508, (May 1980).
Cope, et al., *Analyst,* vol. 107, pp. 611–616, (Jun. 1982).
Kirkbright, et al., *Analyst,* vol. 107, pp. 276–281, (Mar. 1982).

*Primary Examiner*—F. L. Evans
*Assistant Examiner*—Joel L. Harringa

[57] ABSTRACT

A spectroanalytical system includes induction coupled plasma apparatus for exciting sample material to an atomic state for analysis, a source of transport gas, a sample chamber for receiving a sample to be analyzed, and heating means for vaporizing a sample to be analyzed in the chamber and forming particles of the sample of sufficiently small size to form an aerosol. The sample chamber is connected in a flow path between the source of transport gas and the plasma apparatus. A supplemental chamber surrounds the sample chamber, and gas is flowed to the supplemental chamber at a higher rate than the gas flow to the sample chamber. A flow restriction between the sample and supplemental chambers normally permits flow of gas from the supplemental chamber into the sample chamber but also provides pressure relief upon rapid heating for sample vaporization that is effective to minimize pressure transients in the aerosol stream that depress the output signal of the plasma apparatus.

17 Claims, 3 Drawing Figures

SPECTROCHEMICAL ANALYSIS

This invention relates to methods and apparatus for spectrochemical analysis and more particularly to methods and apparatus for preparing analyte materials for transport to suitable excitation sources such as are used with various conventional analytical modes.

The high frequency argon inductively coupled plasma provides an effective excitation source for the simultaneous multielement determination of metals and metalloids over a wide concentration range. Optical emission spectroscopy with the induction coupled plasma source offers detection limits in the parts per billion range for many elements, linear dynamic concentration ranges of typically five orders of magnitude, and freedom for many of the chemical interferences encountered with other sources. The most commonly used technique for introduction of sample solutions into the induction coupled plasma is based on the injection of a liquid aerosol generated by a pneumatic nebulizer. Other sample introduction techniques include electrothermal vaporization devices in which a microliter volume of liquid sample is placed on a heating element remote from the plasma. The heating element is powered by a low voltage, high current power supply fitted with a programmer allowing control of power and time during drying, ashing and vaporization cycles. The vaporized sample material is condensed into aerosol form and then carried into the plasma using a transport gas stream of argon or other suitable inert gas and the transient emission signal at the atomic line of the analyte element is detected.

Principal parameters governing the rate and efficiency of sample transport in such systems are the length of tubing between the heating and excitation units and the flow rate of the transport gas which sweeps the analyte from the heating unit into the plasma source or other excitation unit. The vaporized analyte may be transported effectively over a considerable distance to the excitation unit. While the leading edge of the analyte sample pulse produced by a plasma excitation source is relatively well defined, the passage of the argon carrier gas over the hot graphite rod or other type of heating element gives rise to a pressure pulse which depresses the output signal level of the plasma source.

In accordance with the invention, the aerosol generation and transport path has a pressure relief mechanism which accomodates the thermally generated pressure pulse without loss of vaporized sample to be analyzed, as by exposing the aerosol generation and transport path to a supplemental inert gas at a slight positive pressure so that under normal conditions there is a slight supplemental flow into the transport path, which flow direction is reversed by pressure surges in the carrier gas produced during heating for vaporization of the sample to be analyzed such that those pressure surges do not degrade the base line response of the monochromator or other excitation site monitoring device. In another arrangement, a suitable pressure relief mechanism may be provided by a vent between the transport gas source and the sample chamber, the vent being sized to maintain the desired flow rate of the transport gas between the sample chamber and the excitation unit so that sample is not lost through the vent while accomodating pressure surges in the transport gas produced during thermal vaporization of the sample to be analyzed such that those pressure surges do not depress the output signal of the plasma or other excitation apparatus.

A spectroanalytical system in accordance with the invention is useful for determining the quantity of a substance of interest in a sample material, and includes sample excitation apparatus for exciting sample material to an atomic state for analysis, a source of transport gas, a chamber for receiving a sample to be analyzed, and heating means for vaporizing a sample to be analyzed in the chamber and forming particles of the sample of sufficiently small size to form an aerosol. The chamber is connected in a flow path between the source of transport gas and the sample excitation apparatus, and pressure relief means in the flow path provides pressure relief upon rapid heating of the sample by the heating means to minimize pressure transients in the aerosol stream transported from the chamber to the excitation apparatus.

In particular embodiments, the sample vaporization and transport system includes a heating element for receiving a sample to be analyzed, with a first chamber that surrounds the sample location and that has an inlet for transport gas and an outlet for connection to the sample exciting apparatus for exciting the aerosol sample material to an atomic state. A second chamber surrounds the first chamber, and means for flowing a gas to the second chamber at a higher rate than the gas flow to the first chamber. A flow restriction between the first and second chambers normally permits flow of gas from the second chamber into said first but also provides pressure relief upon rapid $I^2R$ heating of the heating element for sample vaporization that is effective to minimize excitation apparatus output signal depressing pressure transients in the aerosol stream transported from the first chamber to the excitation apparatus.

In accordance with another aspect of the invention, there is provided a method of spectrochemical analysis that includes the steps of providing a flow path that has an inlet connected to a first source of inert gas and an outlet connected to a sample excitation site, rapidly heating sample material to be analyzed disposed on a support element in the flow path to a temperature sufficient to vaporize the sample material, condensing the vaporized material into solid particles of sufficiently small size to form an aerosol, flowing a stream of inert gas from the first source through the flow path during the heating to transport such particles along the flow path to the sample excitation site for spectrochemical analysis, and concurrently providing pressure relief accomodation in the flow path sufficient to prevent depression in the output signal level at said excitation site due to pressure transitions resulting from the rapid heating of the sample material that degrade the spectroanalytical measurement.

In particular embodiments, the electrothermal vaporization (ETV) sample heating rate is greater than 500° C./sec and the sample is heated to a temperature in excess of 1200° C., the transport gas flow rate through the flow path is in the order of 0.1–10 liters/minute, and the pressure relief accomodation includes a supplemental inert gas flow rate that is greater than the flow rate of transport gas through the flow path with a resulting normal flow of supplemental gas into the flow path but such that a pressure transition resulting from the rapid heating of said sample material causes a reversal of flow direction through the supplemental port sufficient to prevent output signal level depression at the plasma sample excitation site. Preferably, in such embodiments, the pressure immediately outside the supplemental port is less than five inches of water greater than the pressure in the flow path.

While the invention may be used with a variety of atomic excitation systems, it is particularly useful with analysis systems that employ excitation systems of the induction coupled plasma (ICP) type.

Other features and advantages of the invention will be seen as the following description of particular embodiments progresses, in conjunction with the drawing, in which.

DESCRIPTION OF PARTICULAR EMBODIMENTS

Figure 1:
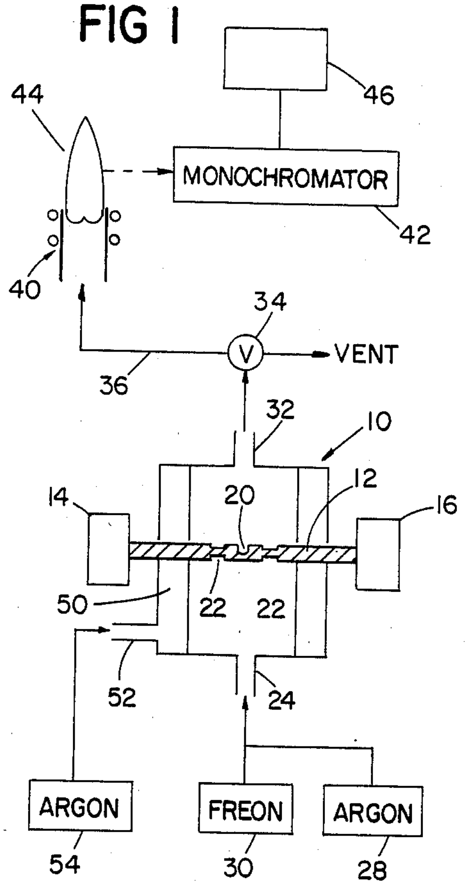
FIG. 1 is a diagrammatic view of a spectrochemical analysis system in accordance with the invention.

The analysis system shown in FIG. 1 includes vaporization chamber 10 in which is disposed vaporizing electrode 12 that is connected between water cooled electrode holding blocks 14, 16. Electrode 12 is fabricated from a commercial 3/16 spectrographic grade graphite rod and includes a crater 20 for receiving the sample to be analyzed. In order to concentrate the heat in crater 20, a section 22 on either side of crater 20 is formed in graphite rod 12. The graphite rod may be treated, as by forming a pyrolytic graphite coating or by applying a tantalum coating. Chamber 10 has an inlet 24 that is coupled to a source of transport gas (argon supply 28 and Freon supply 30). Chamber 10 is a component of a flow path that extends from source 28 through chamber 10 to outlet 32, and then through three-way valve 34 and a one meter length of tygon tubing 36 to induction coupled plasma source 40. The inlet orifice or capillary to the plasma torch 40 has an area of about two square millimeters. Monochromator 42 monitors the plasma plume 44 and provides an output signal to output apparatus 46. Surrounding vaporization chamber 10 is supplemental chamber 50 that has an inlet 52 connected to a source of argon 54.

Figure 2:
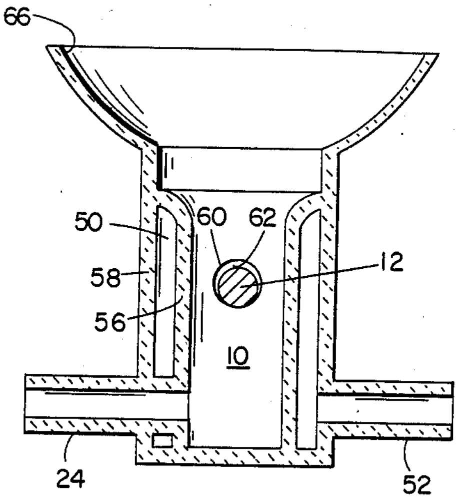
FIG. 2 is a sectional view of the aerosol generating chamber employed in the system shown in FIG. 1.

Further details of the composite chamber structure may be seen with reference to FIG. 2. That double wall quartz structure defines inner electrode chamber 10 (of about thirty milliliters volume) and surrounding outer chamber 50 whose walls 56, 58 are spaced about two millimeters apart. Electrode rod 12 is inserted through support parts 60 (slightly greater than five millimeters in diameter) in concentric chamber walls 56 and 58. A flow restriction gap 62 of about four square millimeters area is formed between each support port 60 and the electrode 12 as indicated in FIG. 2 and permits restricted flow communication between the two chambers 10, 50. Vent gaps of similar area are similarly formed between chamber 50 and the surrounding environment. The inert transport gas flows through inlet 24 (about four millimeters diameter) into inner chamber 10 and the inert supplemental gas flows through inlet 52 (about four millimeters diameter) into outer chamber 50. In use, with transport gas flows at rates of about 0.8–1.6 liters per minute and supplemental gas flows at rates of 3.4–5.5 liters per minute, the resultant gas flows through the chamber outlet 32 are at rates in the range of 2.0–2.5 liters per minute, such that the flow rate into chamber 10 through the two flow restriction gaps 62 is at a rate of about one liter per minute. Other gas flow rates may be used including, for example, an inner chamber gas flow rate of about 0.35 liter per minute and an outer chamber gas flow rate of about 0.5 liter per minute. Sample receiving cup 20 of vaporizing electrode 12 is positioned in the center of chamber 10 and opens upward. The inert gas transport stream flows around the cup 20 and out the top of the chamber through a ball and socket connector (socket 66), into tube 36 and then into the sample inlet of the plasma torch 40.

In use to analyze urine samples, a five microliter sample is deposited in cup 20. The sample is first subjected to a drying temperature at 110° C. and ashing for thirty seconds by heating electrode 12 with a low voltage, high current power supply fitted with a programmer allowing control of power and time during evaporization, ashing and vaporization cycles. Table 1 summarizes analysis conditions used for thirteen elements. Induction coupled plasma (ICP) power levels ranged from 350 watts to 1000 watts, electrothermal vaporization (ETV) temperatures varied between 1600° C. and 2500° C., and inner chamber flow rates varied from 0.8–1.6 liters per minute while outer chamber flow rates varied from 3.4–5.5 liters per minute. Freon-argon mixtures were used for iron, molybdenum, titanium and vanadium. The electrode geometry was changed by varying the depth of the sample receiving cup 20. Comparison with results reported by others indicate that the obtained analysis values and detection limits match well with the best ETV-ICP values reported previously.

Figure 3:
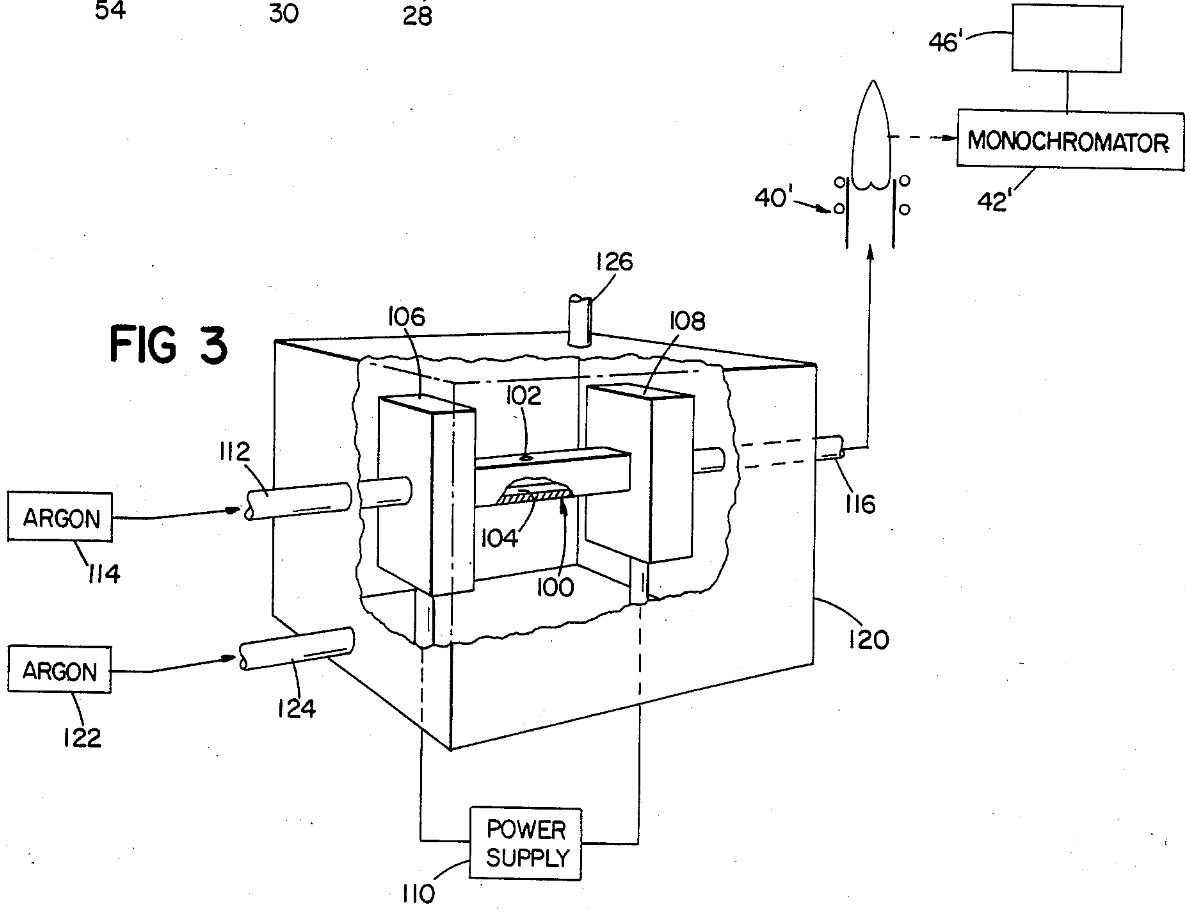
FIG. 3 is a diagram of a second spectrochemical analysis system in accordance with the invention.

Another embodiment is shown in FIG. 3. In that embodiment, the heating element 100 is a rectangular tube of the type disclosed in Dennison et al. U.S. Pat. No. 3,895,873. Tube 100 is of ultradense spectrographic grade graphite, is square in cross section and has a length of about three centimeters, each side of the square having an outside dimension of about 0.6 centimeter and the walls of the graphite tube being about one millimeter thick.

TABLE 1

ELECTROTHERMAL VAPORIZATION - INDUCTIVELY COUPLED PLASMA OPERATING CONDITIONS

| ELEMENT | POWER watts | VAPORIZATION TEMPERATURE °C. | ARGON FLOWS Inside l/m | ARGON FLOWS Outside l/m | ELECTRODE GEOMETRY Depth of Cup 20 mm | WAVELENGTH nanometers |
|---|---|---|---|---|---|---|
| Arsenic | 600 | 2010 | 1.5 | 4.5 | 2.0 | 193.7 |
| Cadmium | 800 | 1600 | 0.8 | 4.0 | 2.0 | 214.4 |
| Chromium | 650 | 2100 | 1.0 | 4.0 | 2.0 | 267.7 |
| Copper | 350 | 2150 | 1.6 | 4.6 | 2.0 | 324.7 |
| Iron | 700 | 2450 | 1.0+ | 4.2 | 3.0 | 238.2 |
| Lead | 570 | 2100 | 1.2 | 4.0 | 2.0 | 220.4 |
| Manganese | 650 | 2080 | 1.5 | 4.8 | 2.0 | 253.6 |
| Molybdenum | 1000 | 2470 | 1.4+ | 5.5 | 3.0 | 313.3 |
| Nickel | 550 | 2450 | 0.8 | 4.5 | 3.5 | 352.5 |

TABLE 1-continued

ELECTROTHERMAL VAPORIZATION - INDUCTIVELY COUPLED PLASMA OPERATING CONDITIONS

| ELEMENT | POWER watts | VAPORIZATION TEMPERATURE °C. | ARGON FLOWS Inside l/m | ARGON FLOWS Outside l/m | ELECTRODE GEOMETRY Depth of Cup 20 mm | WAVELENGTH nanometers |
|---|---|---|---|---|---|---|
| Selenium | 620 | 2080 | 1.3 | 4.3 | 1.5 | 196.0 |
| Titanium | 650 | 2450 | 0.8+ | 4.0 | 3.5 | 334.9 |
| Vanadium | 700 | 2500 | 0.8+ | 3.4 | 3.0 | 309.3 |
| Zinc | 700 | 2000 | 1.4 | 4.4 | 2.0 | 213.9 |

Coolant 16 LPM, Auxiliary 1 LPM, Observation height 16 mm.
Sample cup geometry - 2.5 mm dia.
Drying 110° C., 30 s; ashing 30 s (except for Cu - urine 40 s, resin 50 s)
Vaporization rate 800° C./S
+0.5% chlorodifluoromethane (Freon) in inner gas flow.

Other tubular configurations (cylindrical, for example) and other electrothermal materials such as tungsten or tantalum may be used for heating element 100. Access to the interior of heating element 100 is provided by port 102 that has an area of about one square millimeter and through which a sample is introduced into tube 100 by a micro pipette for deposit on surface 104. Heating element 100 is connected to water cooled electrical contact blocks 106, 108 at each end which are in turn connected to power supply 110. Teflon inlet tube 112 extends from transport gas supply 114 into contact block 106 in communication with heating tube 100 and Teflon outlet tube 116 extends into contact block 108 and provides communication between heating element 100 and ICP torch 40' that is monitored by associated monochromator 42'. Housing 120 encloses the heating element 100 and contact block members 106, 108, and has a vent 126. Supplemental inert gas from source 122 is supplied to housing 120 through conduit 124.

In operation, a sample to be analyzed is introduced through port 102 into heating tube 100. The outer chamber 120 is closed and pressurized to about three inches of water with a flow of argon from source 122 at a rate of about three liters per minute and sample transport argon is flowed through the heating element 100 at a rate of about one-half liter per minute, pressurizing tube 100 to about two inches of water. Application of electrical power from supply 110 through contacts 106, 108 and heating tube 100 heats the walls of the tube 100 rapidly. The pressure pulse due to that rapid heating is dissipated by gas flow reversal through the coupling between tube 100 and chamber 120 via port 102 sufficient to prevent depression in the output signal level from the plasma plume that degrades the spectroanalytical measurement by monochromator 42' and output unit 46'. Analytical results similar to those described above in connection with the embodiment shown in FIGS. 1 and 2 are obtained.

While particular embodiments of the invention have been shown and described, various modifications will be apparent to those skilled in the art and therefore it is not intended that the invention be limited to the disclosed embodiments or to details thereof, and departures may be made therefrom within the spirit and scope of the invention.

What is claimed is:

1. A spectroanalytical system for determining the quantity of a substance of interest in a sample material comprising sample excitation apparatus for exciting sample material to an atomic state for analysis, means for monitoring said sample excitation apparatus, a source of transport gas, a sample chamber for receiving a sample to be analyzed, heating means for vaporizing a sample to be analyzed in said sample chamber and forming particles of said sample of sufficiently small size to form an aerosol, said sample chamber being connected in a flow path between said source of transport gas and said sample excitation apparatus, and pressure relief means in said flow path for relieving pressure increases resulting from rapid heating of said sample by said heating means to minimize pressure transients in the aerosol stream transported from said chamber to said excitation apparatus, said pressure relief means including structure defining a flow restriction passage between a location external to said flow path and said sample chamber, said flow restriction passage normally permitting gas flow from said location external to said flow path into said sample chamber but also permitting a reversal of gas flow direction through said flow restriction sufficient to prevent output signal level depression at said sample excitation apparatus.

2. The system of claim 1 wherein said sample excitation apparatus includes an induction coupled plasma source.

3. The system of claim 2 wherein said means for monitoring said induction coupled plasma source includes a monochromator.

4. The system of claim 1 wherein said heating means includes a sample holder formed of electrothermal material, said sample holder having a sample receiving region, and contact structure connected to said sample holder on opposite sides of said sample receiving region for supplying electrical current for flow through said sample holder to provide $I^2R$ heating of said sample receiving region.

5. The system of claim 4 wherein said sample holder is of graphite.

6. A spectroanalytical system for determining the quantity of a substance of interest in a sample material comprising sample excitation apparatus for exciting sample material to an atomic state for analysis, means for monitoring said sample excitation apparatus, a source of transport gas, a sample chamber for receiving a sample to be analyzed, heating means for vaporizing a sample to be analyzed in said sample chamber and forming particles of said sample of sufficiently small size to form an aerosol, said sample chamber being connected in a flow path between said source of transport gas and said sample excitation apparatus, and pressure relief means in said flow path for relieving pressure increases resulting from rapid heating of said sample by said heating means to minimize pressure transients in the aerosol stream transported from said chamber to said excitation apparatus, said pressure relief means including a second chamber surrounding said sample chamber, means for flowing a gas to said second chamber to create a pressure in said second chamber that is higher than the pressure in said sample chamber, and a flow restriction between said sample and second chamber that normally permits flow from said chamber into said sample chamber but also permits a reversal of flow direction through said flow restriction sufficient to prevent output signal level depression at said sample excitation apparatus.

7. The system of claim 6 wherein the pressure in said second chamber is less than five inches of water greater than the pressure in said sample chamber.

8. The system of claim 7 wherein said sample excitation apparatus includes an induction coupled plasma source.

9. The system of claim 8 wherein said means for monitoring said induction coupled plasma source includes a monochromator.

10. The system of claim 9 wherein said sample chamber includes a member of electrothermal material, said member having a sample receiving region, and said heating means includes contact structure connected to said member on opposite sides of said sample receiving region for supplying electrical current for flow through said member to provide $I^2R$ heating of said sample receiving region.

11. The system of claim 10 wherein said member is of graphite.

12. A method of spectrochemical analysis comprising the steps of providing a flow path that has an inlet connected to a source of inert gas and an outlet connected to a sample excitation site, disposing sample material to be analyzed on a support element in said flow path, rapidly heating sample material to be analyzed disposed on said support element to a temperature sufficient to vaporize said sample material, condensing said vaporized material into solid particles of sufficiently small size to form an aerosol, flowing a stream of inert gas from said source through said flow path during said heating to transport such particles along said flow path to said sample excitation site for spectrochemical analysis, and providing concurrent pressure relief accommodation in said flow path by flowing supplemental inert gas into said flow path through a supplemental port at a rate such that a pressure transition resulting from the rapid heating of said sample material causes a reversal of the direction of flow through said supplemental port sufficient to prevent depression in the output signal level at said excitation site due to pressure transitions resulting from the rapid heating of said sample material.

13. The method of claim 12 wherein said sample is heated at a rate greater than 500° C./sec to a temperature in excess of 1200° C.

14. The method of claim 12 wherein the flow rate of inert gas through said flow path from said source is in the order of 0.1–10 liters/minute.

15. The method of claim 12 wherein said supplemental inert gas is supplied to said supplemental port at a flow rate greater than the flow rate of inert gas from said source through said flow path.

16. the method of claim 12 wherein the pressure immediately outside said supplemental port is less than five inches of water greater than the pressure in said flow path.

17. The method of claim 16 wherein said sample excitation site includes an induction coupled plasma source that is connected to said flow path.

* * * * *